United States Patent
Huang et al.

(10) Patent No.: US 12,185,655 B2
(45) Date of Patent: Jan. 7, 2025

(54) METHOD FOR MICRO-RIDGE MIXED-SOWING CULTIVATION OF DRYLAND CROPS

(71) Applicant: Hunan Agriculture University, Changsha (CN)

(72) Inventors: Huang Huang, Changsha (CN); Yin Zhang, Changsha (CN); Jingyi Li, Changsha (CN); Ren Wang, Changsha (CN); Xiangsheng Gong, Changsha (CN); Zhiqiang Fu, Changsha (CN); Can Chen, Changsha (CN); Zhengjun Yu, Changsha (CN); Yugang Liang, Changsha (CN); Jiaolong Ding, Changsha (CN); Xiangjie Meng, Changsha (CN); Dan Wu, Changsha (CN); Yao Huang, Changsha (CN); Xiaolan Liao, Changsha (CN)

(73) Assignee: Hunan Agriculture University, Changsha (CN)

( * ) Notice: Subject to any disclaimer, the term of this patent is extended or adjusted under 35 U.S.C. 154(b) by 806 days.

(21) Appl. No.: 17/429,624

(22) PCT Filed: Apr. 26, 2021

(86) PCT No.: PCT/CN2021/089806
§ 371 (c)(1),
(2) Date: Aug. 9, 2021

(87) PCT Pub. No.: WO2022/028010
PCT Pub. Date: Feb. 10, 2022

(65) Prior Publication Data
US 2022/0304222 A1    Sep. 29, 2022

(30) Foreign Application Priority Data

Aug. 6, 2020   (CN) .......................... 202010782455.9

(51) Int. Cl.
*A01C 21/00*     (2006.01)
*A01B 39/14*     (2006.01)
(Continued)

(52) U.S. Cl.
CPC ............ *A01C 21/005* (2013.01); *A01B 39/14* (2013.01); *A01G 22/22* (2018.02); *A01K 67/02* (2013.01)

(58) Field of Classification Search
CPC ...... A01C 21/005; A01G 22/22; A01B 39/14; A01K 67/02
See application file for complete search history.

(56) References Cited

FOREIGN PATENT DOCUMENTS

CN    109511478 A   *   3/2019  ............... A01C 1/00
CN    111919681 A   *  11/2020  ............. A01B 39/14
(Continued)

*Primary Examiner* — Tara Mayo
(74) *Attorney, Agent, or Firm* — Bayramoglu Law Offices LLC

(57) ABSTRACT

A method for micro-ridge mixed-sowing cultivation of dryland crops includes the following steps: S1: cleaning ditches and draining away water in dryland; S2: harvesting the preceding crop, leaving the stubble, smashing the stalks of the preceding crop, and then spreading the smashed stalks on the stubble; S3: trenching the dryland to form ecological trenches; S4: flattening the standing stubble and the smashed stalks on the seedbed surface to form an underlying surface, molding seed-fertilizer-soil compounds into a ridge shape and allowing the seed-fertilizer-soil compounds to fall on the underlying surface to form ecological ridges, wherein a plurality of ecological ridges are formed between adjacent ecological trenches, an ecological depression is formed between adjacent ecological ridges, and after sowing, an irrigation is carried out, including: draining water shortly after the irrigation, without leaving a water layer in the field.

20 Claims, 1 Drawing Sheet

(51) Int. Cl.
*A01G 22/22* (2018.01)
*A01K 67/02* (2006.01)

(56) References Cited

FOREIGN PATENT DOCUMENTS

CN 111919688 A * 11/2020 ............. A01G 22/22
GB 362226 A * 12/1931 ............. A01G 24/60

* cited by examiner

METHOD FOR MICRO-RIDGE MIXED-SOWING CULTIVATION OF DRYLAND CROPS

CROSS REFERENCE TO THE RELATED APPLICATIONS

This application is the national phase entry of International Application No. PCT/CN2021/089806, filed on Apr. 26, 2021, which is based upon and claims priority to Chinese Patent Application No. 202010782455.9, filed on Aug. 6, 2020, the entire contents of which are incorporated herein by reference.

TECHNICAL FIELD

The present invention relates to a cultivation method for dryland crops, and in particular to a method for micro-ridge mixed-sowing cultivation of dryland crops.

BACKGROUND

The agricultural resources and environment in China are facing threats consisting of both exogenous pollution and endogenous pollution. In China, non-point source pollution caused by agriculture has already overtaken that from industries as a bottleneck for sustainable agricultural development. According to statistics, in 2018, the use of chemical fertilizers and pesticides in China reached 60 million tons and 300,000 tons (obtained after multiplying their NPK contents), respectively, but the utilization rate of chemical fertilizers was only about 35%. The high level of pesticide residue attendant upon the use of pesticides leads to soil degradation, nutrient loss, resource waste, environmental pollution, and reduced product quality. In China, the sown area of dryland crops for an average year exceeds 66.67 million ha, and the total yield of dryland crops exceeds 400 million tons. Estimated according to the grain-to-stalk ratio of 1:1.2, the annual production of dryland crop stalks exceeds 480 million tons. A stalk contains a large number of organic matters, nutrient elements such as nitrogen (N), phosphorus (P) and potassium (K), and other macro-elements and micro-elements. The N, P and K nutrient content in the 480 million tons of stalks amounts to 4 million tons of urea, 6 million tons of superphosphate, and 6 million tons of potassium sulfate. Therefore, the two measures, including dry direct-seeding without tillage and stalk fertilizer utilization, when put into practice, would produce significant fertilizer saving effects, thereby vigorously promoting green development. At present, dryland crop stalks in China are prohibited from being directly burned or discarded in random piles. When used as organic fertilizer, the stalks are generally digested in situ, that is, after the dryland crop grains are harvested, the stubble and smashed stalks are left in situ to be shallowly buried by ploughing. In recent years, China has witnessed an increase in the yields of dryland crops and stalks. In this regard, if not buried shallowly, the stalks would disturb direct no-tillage, thereby affecting sowing quality. Therefore, in the context of returning dryland crop stalks to dryland in situ, how to realize no-tillage sowing remains a problem to be solved urgently. The solution to this problem plays a key role in improving the utilization rate of stalks and conservation tillage practices.

An increase in the utilization rate of chemical fertilizers and pesticides can produce significant direct and indirect benefits. For instance, a one-percentage-point increase in the fertilizer utilization rate can lead to a reduction of 454,500 tons in the use of urea, a reduction of 217,300 tons in the nitrogen emission, and a saving of 454,500 tons in coal, thereby cutting down the production input by about 818 million CNY. It also facilitates reducing pesticide residues, safeguarding the quality and safety of agricultural products, and protecting the soil and water environment. Returning crop stalks to dryland in situ or by mulching can effectively increase the crop yield, generally by more than 4%.

SUMMARY

The present invention provides a method for micro-ridge mixed-sowing cultivation of dryland crops to solve the following technical problems: that is, to overcome the problem that returning stalks to dryland not only affects tillage during the production of dryland crops but also has a low utilization rate, the consumption of chemical fertilizers is high, and the topdressing time and application amount are unreasonable; to avoid the influence of the basal application of fertilizers on sowing; and to improve the seedling emergence rate and percentage of dryland crops without tillage. This method can increase the fertilizer utilization rate and reduce the consumption of pesticides based on the premise of no-tillage and dry seeding, thereby saving fertilizers, reducing costs, and improving soil fertility.

To solve the above-mentioned technical problems, the present invention adopts the following technical solutions.

A method for micro-ridge mixed-sowing cultivation of dryland crops includes the following steps:

S1: cleaning ditches and draining away water in dryland;

S2: harvesting a preceding crop, leaving the stubble, smashing the stalks of the preceding crop, and then spreading the smashed stalks on the stubble;

S3: trenching the dryland to form ecological trenches; and

S4: flattening the standing stubble and the smashed stalks on the seedbed surface to form an underlying surface; molding seed-fertilizer-soil compounds into a ridge shape and falling the seed-fertilizer-soil compounds on the underlying surface to form ecological ridges, wherein a plurality of ecological ridges are formed between adjacent ecological trenches, an ecological depression is formed between adjacent ecological ridges, and after sowing, an irrigation is carried out once in a manner, wherein the manner includes: draining water shortly after the irrigation, without leaving a water layer in the field; wherein the seed-fertilizer-soil compounds are obtained by thoroughly mixing soil with seeds of the dryland crops and chemical fertilizers.

The core underlying the technical principle of the present invention is the formation of the ecological ridges, ecological depressions, and ecological trenches. Composed of organisms, nutritive bodies, and water and soil bodies, the ecological ridges have the following two functions of: (1) serving as a medium to wrap the organisms and the nutritive bodies, physically protecting the integrity of the organisms and the nutritive bodies, preserving heat and moisture, and providing water and air permeability; and (2) serving as a donor to provide water and nutrients for the organisms and the nutritive bodies. The ecological depressions are composed of a sponge layer, a topsoil layer and ecological cracks to provide storage capacity for the ecological ridges, while regulating water, fertilizers, air, temperature and humidity in the ecological ridges. The ecological trench is composed of a trench body, side cracks, and bottom mud. The ecological trenches have the functions of draining and irrigating, providing raw materials for the ecological ridges, and providing channels for aquatic animals, so that loach, eel, field snails and the like can be bred in the ecological trenches to eliminate pests and weeds for dryland crops. In the state of no-tillage and dry direct-seeding without irrigation, radicles and germs emerging from the seeds in the ecological ridges enjoy superior temperature and humidity conditions and absorb nutrients in the seeds and compounds, thus growing faster than the weed seeds inside and outside the ridges, and growing roots and leaves more smoothly. On the basis of conventional dryland management, within 15-50 days after the seedling emergence of dryland crops, young chickens with blindfolds are put to prevent and control diseases, pests and weeds. By no-tillage and dry direct-seeding with fertilizers and soil, the present invention significantly improves the seedling emergence percentage, the growth rate at the seedling stage, and the ability of crop plants to suppress weeds, thereby realizing zero pesticide input at the seedling stage and the middle stage of the crops, while improving the utilization rate of water and fertilizers as well as temperature and light.

Further, in S4, the ecological ridge is a trapezoid with a bottom width of 5.5 to 11.5 cm, a top width of 1.5 to 5.5 cm, and a height of 3.5 to 9.5 cm.

In the above solution, in comparison between micro-ridge mixed-sowing and hole sowing, hole sowing uses a machine to dig holes for sowing seeds, whereas micro-ridge mixed-sowing is to mix seeds, fertilizers, and soil into compounds, spread the compounds on the underlying surface, and then uses a shaper to mold the compounds into a ridge shape. The trapezoid is narrow at the top and wide at the bottom to form a long ridge shape, with the same length as a plot in the dryland. The bottom of the trapezoid is seamlessly connected to the underlying surface, so that not only can water from the soil surface be channeled into the ridges under capillary action, but also can the excess unbound water in the ridges be drained to the soil surface of the dryland.

Further, in S4, the mass ratio of the seeds of the dryland crops, the chemical fertilizers and the soil is 6 to 14:50 to 70:6,000 to 20,000.

Gathering fertilizers and moisturizing seedlings: since the ecological ridge is formed by mixing the seeds, the chemical fertilizers, and the soil thrown up during trenching at a mass ratio of 6 to 14:50 to 70:6,000 to 20,000, the chemical fertilizers account for nearly 1% of the ecological ridge, and are evenly distributed to turn the ecological ridge into fertile soil. Therefore, the ecological ridge gathers a small amount of chemical fertilizer to become fertile soil to promote the growth of seedlings.

Further, in S3, the spacing between the adjacent ecological trenches is 2 to 6 m, and the ecological trench has a depth of 45 to 85 cm and a width of 10 to 18 cm.

Further, the amount of the seeds in S4 is 3 to 105 kg/ha. The vast majority of seeds do not need to be soaked in water for accelerating germination, but a small minority of seeds, such as celery, need to be soaked for accelerating germination before sowing.

Further, the soil in S4 is soil thrown up during trenching in S3.

Further, in S1, ditch cleaning and drainage are carried out at the maturity stage of the preceding crop until the dryland is in a state allowing a harvester to operate.

Further, the method for micro-ridge mixed-sowing cultivation of dryland crops further includes S5: within 15 to 50 days after the seedling emergence of dryland crops, putting 600 to 900 6-to-8-week-old chickens with blindfolds per ha, and feeding the young chickens with special feed at the early stage of free-range rearing; wherein after adapting to the environment of the dryland, the young chickens obtain food mainly by grazing in the dryland, supplemented by food feeding. The young chickens are blindfolded and thus can only see the ground to mainly eat pests and feed instead of the dryland crops.

Further, the spacing within and between rows of the dryland crops during cultivation is 5 to 45 cm×10 to 80 cm, and the spacing within and between rows of the dryland crops during seedling cultivation is 1 to 3 cm×2 to 6 cm.

Micro-ridge mixed-sowing can be used for not only no-tillage and dry direct-seeding, but also as a way of cultivating seedlings. When the micro-ridge mixed-sowing is used for cultivating seedlings, the spacing within and between rows shall be changed accordingly to 1 to 3 cm×2 to 6 cm. In this way, during transplanting, the seedlings can be lifted directly with soil, which is not only convenient for operation but also guarantees the quality of transplanting.

Seedlings supporting for the growth of standing stalks: after sowing, a high concentration of chemical fertilizers in the ecological ridges accelerates the growth of seedlings, and promotes the rapid and robust growth of rice during the seedling stage of dryland crops, so that the stems and leaves above ground and the underground root system rapidly expand to effectively suppress the growth of weed roots, stems and leaves, which is conducive to the early growth of strong standing stalks. Particularly, the sown seeds are provided with certain water, temperature, air and humidity conditions, while the weed seeds are still in a dormant state. The early and rapid start of dryland crop growth and the late and slow start of weed growth create a difference in their growth, which is conducive to suppressing the growth of weeds by the growth of dryland crops as well as suppressing the growth of roots, stems and leaves of weeds by the growth of roots, stems and leaves of the dryland crops.

Further, in S3, a chain trencher is used for trenching.

In S4, the standing stubble and the smashed stalks are flattened by using a warped pressing plate.

In S4, the seed-fertilizer-soil compounds pass through a drop guide before falling to the underlying surface, the drop guide conveys the scattered seed-fertilizer-soil compounds to the shaper, and then the trapezoid is formed through the shaper to fall on the underlying surface.

The warped pressing plate is used to spread the standing stubble and the smashed stalks on the seedbed surface between the trenches, and to flatten the stubble and the smashed stalks to form a relatively flat underlying surface. The seed-fertilizer-soil compounds are spread in strips on the underlying surface. Before falling on the underlying surface, the seed-fertilizer-soil compounds pass through the drop guide, and then the drop guide conveys the fallen seed-fertilizer-soil compounds to the shaper. After passing through the shaper and falling down, the seed-fertilizer-soil compounds form trapezoids each with a wide bottom and a narrow top, thus forming a row of micro-ridges. During operation, the micro-ridge mixed-sowing machine completes, at one time, stubble flattening and spreading, trenching and soil taking, seed-fertilizer-soil mixing, and discharge of the seed-fertilizer-soil compounds in strips into the ridges.

A seed-fertilizer-soil compound conveyor, a fertilizer apparatus, a seeding apparatus, a spiral seed-fertilizer-soil compound discharge apparatus and the like are all driven by DC motors, respectively. The drop guide and the shaper have no driving device, relying on gravity, the kinetic energy of the machine during forward movement, and the coupling with the drop guide and the shaper to guide the falling and carry out the shaping for the seed-fertilizer-soil compounds.

Casting soil into fertilizers: the chain trencher throws up the soil in the trench to turn the soil into crushed soil, so that most of the soil becomes powder, which is conducive to the release of nutrients for the roots of the seedlings to absorb, thereby turning the soil into fertilizers.

In the above solution, diseases, pests and weeds in the dryland are controlled mainly by young chickens, but when diseases and pests of dryland crops break out over a large area, biological insecticides shall be used timely for prevention and control.

It is necessary to observe the growing state of the chickens every evening, to prevent the chickens from escaping and being injured by their natural enemies. The feeding amount of the chickens increases as the food intake of the chickens increases.

In the above solution, the micro-ridge mixed-sowing shall be carried out in sunny or cloudy days immediately or in light rainy days in the later period. Meanwhile, the drainage outlet shall be opened in rainy days to prevent water accumulation in the dryland.

In the above solution, when sowing the seed-fertilizer-soil compounds, the seeds and the fertilizers are evenly mixed with the soil to ensure that the seeds can easily absorb nutrients, while preventing the seed buds from being damaged by the excessively high concentration of chemical fertilizers under the action of the soil in the ridges. In the early stage of germination, the seed roots are isolated by the soil and thus do not come into contact with the chemical fertilizers or other seeds, and the nutrients released after the decomposition of the chemical fertilizers can be absorbed by the roots through the soil in the ridges.

In the present invention, the soil in the dryland is removed to form ecological trenches, and the removed soil is mixed with the stubble, the stalks smashed by the harvester, the chemical fertilizers, and the selected seeds to form compounds for micro-ridge mixed-sowing. With the help of the warped pressing plate for flattening the stalks, a relatively flat underlying surface is constructed. The seed-fertilizer-soil compounds are discharged through the spiral outlet of the fertilizer applicator and the seeder (i.e., the fertilizer apparatus and the seeding apparatus), and then pass through the shaper to become ridges, where an ecological depression is formed between two ridges. A configuration including the ecological ridges, the ecological depressions and the ecological trenches which are distributed orderly is formed on the water level. On the vertical plane, a seed material layer (seeds, fertilizers and soil), a stalk layer, a topsoil layer, and an exchange layer are formed from top to bottom to form a three-dimensional configuration in which water, air and fertilizers in the soil plough layer are coordinated and integrated to realize the early emergence of seedlings and the emergence of a full stand of seedlings and strong seedlings. The seeds are sown in the no-tillage dryland to maintain the plough layer structure of the dryland, thereby maintaining the stability of the dryland ecosystem. The stalks are fully returned to the dryland for utilization to reduce environmental pollution, thereby realizing highly-efficient recycling and utilization of agricultural resources. There are three sources of water for the seeds during germination: water from the seeds themselves, water in the ridges, and water entering the ridges under capillary action from the soil surface. There are three water retention barriers: the peel and the seed coat, the soil micro-aggregates attached to the surface of the grain, and the soil in the ridges, which provide more ways for the seeds to absorb water, thereby reducing the impact of unfavorable factors in the external environment, and solving the problem that dryland crops by direct seeding cannot ensure a full stand of the emerging seedlings. As being uniformly distributed in the ridges, the compound fertilizers can be effectively utilized by the seeds, so that the seedlings can quickly absorb nutrients to facilitate the formation of vigorous seedlings and strong seedlings. Chickens are adopted to control diseases, pests and weeds in the dryland, while reducing the use of pesticides, thereby realizing green production. In the middle and late stages of the growth of dryland crops, a topdressing principle adapted to the seedlings and the dryland is adopted to reduce the consumption of chemical fertilizers and improve its utilization rate, while ensuring the normal growth of dryland crops.

With the ecological ridges formed by the crushed soil during immediate trenching, the ecological depressions formed between the ecological ridges, and the ecological trenches formed after throwing up the crushed soil, by means of no-tillage and dry direct-seeding with fertilizers and soil, the present invention significantly increases the seedling emergence percentage, remarkably increases the growth rate at the seedling stage, and remarkably enhances the weed suppression ability of the crop plants, thereby realizing zero pesticide input at the seedling stage and the middle stage, while improving the utilization rate of water and fertilizers as well as temperature and light.

The ecological ridges are composed of organisms, nutritive bodies, and water and soil bodies. The organisms are seeds that are uniformly distributed and wrapped in the ridges. The nutritive bodies are compound fertilizer granules that are not connected to the seeds, but are evenly distributed among the organisms. The water and fertilizer bodies are dryland soil with 10% to 70% water content to be thrown up by the trencher. The ecological ridges have the following two functions of: (1) serving as a medium to wrap the organisms and the nutritive bodies, physically protecting the integrity of the organisms and the nutritive bodies, preserving heat and moisture, and providing water and air permeability; and (2) serving as a donor to provide water and nutrients for the organisms and the nutritive bodies.

The ecological depressions are composed of a sponge layer, a topsoil layer and ecological cracks. The sponge layer is the stalks left after the preceding crop is harvested, including the standing stubble which is flattened and the smashed stalks which are discharged by the harvester, so as to jointly form a spongy structure. The topsoil layer is located beneath the stalk layer, serves as a plough layer for the growth of dryland crops, provides storage capacity for the ecological ridges, and regulates water, fertilizers, air, temperature and humidity in the ecological ridges. The ecological cracks are located in the ecological depressions, and are cracks in the dryland. The ecological cracks serve as channels to convey oxygen and exhaust other gases. The ecological cracks are communicated with each other and are communicated with the ecological trenches to form a drainage network of the dryland.

The ecological trench is composed of a trench body, side cracks, and bottom mud. As the main structure of the trench, the trench body is a rectangular solid to accommodate water. When the trench is full of water, the rectangular solid completely accommodates the water. When the trench is half full of water, the upper half of the rectangular solid is used for accommodating air, while the lower half of the rectangular solid is used for accommodating the water. The ecological trenches have the functions of draining and irrigating, providing raw materials for the ecological ridges, and providing channels for aquatic animals, so that loach, eel, field snails, and the like can be bred in the ecological trenches.

Compared with the prior art, the present invention has the following advantages.
(1) Labor saving function: the present invention realizes direct-seeding of dryland crops without tillage, thereby saving labor required by tillage.
(2) Stalk cleaning function: after the stalks are completely returned to the dryland, it is difficult to carry out mechanical rotary tillage or ploughing. As a result, farmers have to exchange time for space, that is, to lay aside for a few days, allowing the stalks to naturally lose water and wilt to facilitate operation, which delays the farming season. In the present invention, the stalks of the preceding crop are spread on the surface of the dryland to form an underlying surface, which not only protects the surface layer of the dryland, but also provides a rhizosphere environment for the growth of the dryland crops at the seedling stage, thereby returning the stalks to the dryland while improving resource utilization.
(3) Oxygen enrichment function: oxygen for the dryland crops is supplied by utilizing the thin seal of the ecological ridges and the air permeability function of the over-ground part.
(4) Function of protecting and strengthening seedlings: the micro-ridge mixed-sowing can increase ways for the seeds to absorb water while promoting the germination and seedling emergence of the seeds. The ecological depressions and the ecological trenches have the same length, and are adjacent but not connected. Under the capillary action and the fine crack action of the dryland, the subsurface water is drained when there is excess water, and water is retained in case of deficiency. An appropriate amount of fertilizer is mixed in the ridge-shaped soil wall, so that the seedlings can quickly absorb nutrients, which is conducive to the formation of vigorous and strong seedlings.
(5) Function of weed prevention and control: at the seedling stage of dryland crops, weed prevention and control is mainly based on a high position formed by the ecological ridges, supplemented by the shading effect formed by the growth of dryland crops. In the middle stage of the growth of dryland crops, the weeds in the dryland are controlled mainly based on the shading effect formed by the growth of dryland crops, supplemented by the physical control of the ecological ridges. The chickens are used to control the weeds during the combined farming of the dryland crops and the chickens.
(6) Functions of fertilizer saving and high yield: an appropriate amount of basal fertilizer is applied, and then fertilizers are applied depending on seedlings and moisture at the middle and later stages of the growth of dryland crops. Particularly, 70% to 90% of the total amount of chemical fertilizers, has been applied to the ecological ridges during sowing, thereby avoiding problems such as high consumption of chemical fertilizers due to volatilization loss, and unreasonable topdressing. The basal fertilizer applied at the early stage of the growth of dryland crops is beneficial to the formation of strong seedlings, and the topdressing at the middle and the later stages depending on seedlings and moisture creates the best condition for the growth of dryland crops, so as to lay a foundation for high yield of dryland crops.
(7) Function of improving the utilization rate of agricultural resources: the direct-seeding in the ecological ridges realizes precise quantification of the seeds and the basal fertilizer as well as precise positioning of the sowing position to avoid the disordered state of dryland crops by traditional direct-seeding and fertilizers applied in a spread manner, thereby saving seeds and fertilizers. The basal fertilizer can supply nutrients most directly and rapidly at the early stage of the growth of dryland crops to gradually act on the plant root system at the middle and later stages of the growth of dryland crops, which is conducive to the absorption and growth of the root system of dryland crops, while improving the utilization rate of fertilizers.
(8) Function of ecological benefits: the consumption of pesticides is reduced, the energy consumption during operation is reduced, the burning of stalks is eliminated, and the occurrence of smog is lessened. The structure of the plough layer in the dryland is maintained, and the biodiversity of the dryland and the stability of the ecosystem are maintained.

DETAILED DESCRIPTION OF THE EMBODIMENTS

Figure 1:
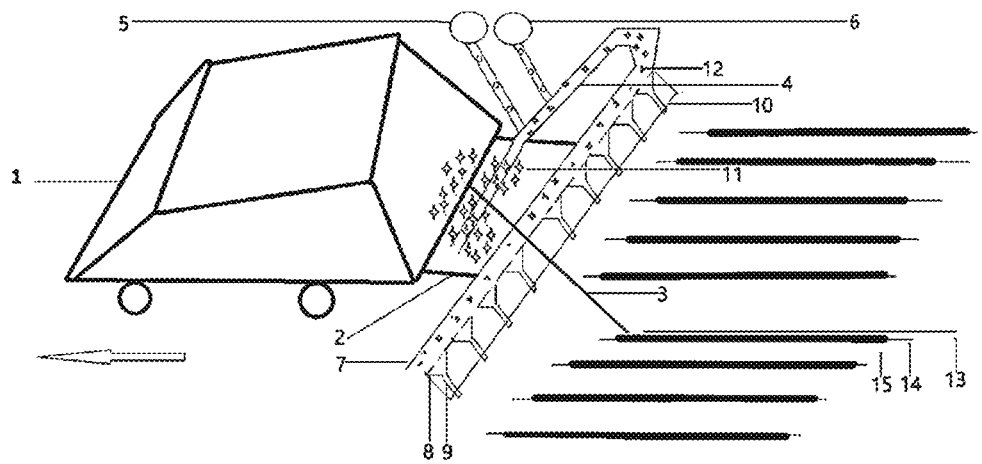
FIG. 1 is a schematic diagram of the structure of the micro-ridge mixed-sowing machine.
Figure 2:
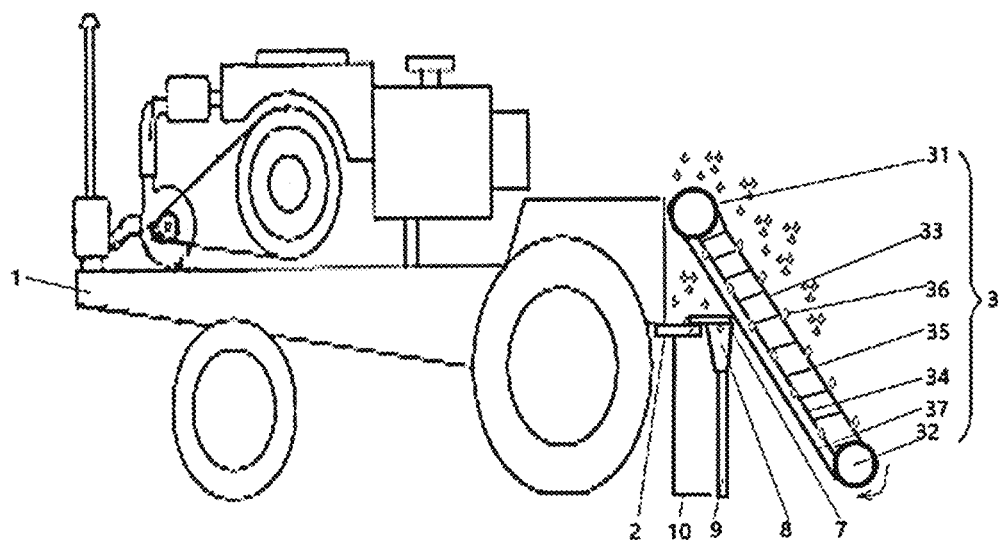
FIG. 2 is a side view of the micro-ridge mixed-sowing machine.

As shown in FIG. 1 to FIG. 2, a micro-ridge mixed-sowing machine includes the tractor 1 and the link rod 2 fixedly connected to the rear of the tractor 1. The arrow in FIG. 1 indicates the heading direction of the tractor 1. The rear of the tractor 1 refers to the direction opposite to the arrow. The tractor 1 is provided with a first driving device connecting to one end of the chain trencher 3. The chain trencher 3 is arranged obliquely. The upper end of the chain trencher 3 is connected to the first driving device, and the lower end of the chain trencher 3 is in contact with the ground. The chain trencher 3 includes the driving wheel 31, the driven wheel 32, the first unloaded chain 33, the second unloaded chain 34, the chain beam 35, the scraper 36 and the load chain 37. The first unloaded chain 33 and the second unloaded chain 34 are arranged between the driving wheel 31 and the driven wheel 32 in a winding manner. There are multiple chain beams 35, which are arranged between the first unloaded chain 33 and the second unloaded chain 34. The scraper 36 is fixed outside the first unloaded chain 33 and the second unloaded chain 34. The load chain 37 is also arranged between the driving wheel 31 and the driven wheel 32 in a winding manner. The first driving device is connected to the driving wheel 31. The first driving device drives the driving wheel to rotate, thereby driving the driven wheel, the first unloaded chain, the second unloaded chain, and the load chain to rotate. The scraper digs trenches in the soil and throws up the soil. The operating parameters of the chain trencher 3 include: a trench spacing of 2-6 m, a trench depth of 45-65 cm, and a trench width of 10-18 cm.

The conveyor 4 is arranged below the chain trencher 3. The upper end of the conveyor 4 is not closed to be used for receiving the thrown soil, and the conveyor 4 adopts a spiral impeller. The conveyor 4 is connected to the fertilizer apparatus 5 and the seeding apparatus 6. The conveyor 4, the fertilizer apparatus 5 and the seeding apparatus 6 are respectively driven by a second driving device, a third driving device, and a fourth driving device which are arranged on the tractor 1. The other end of the conveyor 4 is connected to the screw conveyor 7. The screw conveyor 7 is fixed on the link rod 2. The screw conveyor 7 is driven by a fifth driving device which is arranged on the tractor 1.

The bottom of the screw conveyor 7 is sequentially connected to the drop guide 8 and the shaper 9 from top to bottom. There are multiple sets of drop guides 8 and shapers 9. The shaper 9 is a trapezoid with a bottom width of 5.5 to 11.5 cm, a top width of 1.5 to 5.5 cm, and a height of 3.5 to 9.5 cm. The distance between two adjacent sets of drop guides 8 and shapers 9 is 4-6 cm.

The warped pressing plate 10 includes a warped end and a horizontal end. The warped end is fixed to the link rod 2, and the horizontal end is parallel to the ground and close to the ground. The warped pressing plate 10 is L-shaped. The warped end is perpendicular to the horizontal end.

The conveyor, the fertilizer apparatus, the seeding apparatus, and the screw conveyor are all driven by DC motors, respectively. The drop guide and the shaper have no driving device, relying on gravity, the kinetic energy of the machine during forward movement, and the coupling with the drop guide and the shaper to guide the falling and carry out the shaping for the seed-fertilizer-soil compounds.

Embodiment 1

From October 2019 to May 2020, micro-ridge mixed-sowing cultivation of oilseed rape was implemented in the Quantang Subdistrict, Mingyue Village, Lukou Town, Changsha County, Changsha city, Hunan province, China:
1. The preceding crop was rice, which was harvested on October 27. The trenches were cleaned on that day, and the soil was dry, which is suitable for the operation of the four-wheel tractor.
2. The stubble and stalks left after harvesting the rice were not removed to serve as a rhizosphere layer for the growth of oilseed rape.
3. As shown in FIG. 1, sowing is carried out by using the micro-ridge mixed-sowing machine: 1) the chain trencher is used for trenching to throw up the soil in the field to form trenches. The trench spacing is 8 m, the trench depth is 55 cm, and the trench width is 12 cm. Most of the thrown soil becomes the raw materials for mixed-sowing. The materials for sowing are composed of compounds of rice seeds, chemical fertilizers, and the soil thrown up during trenching. During sowing, the oilseed rape seeds, the chemical fertilizers, and the soil thrown up during trenching are mixed at a mass ratio of 0.7:40:8,400 by using the conveyor of the micro-ridge mixed-sowing machine. The consumption of seeds is 5.25 kg per ha, and the seeds are mixed with 20 kg of compound fertilizer having an N:P:K ratio of 25:7:8 and soil to be sown. During operation, the micro-ridge mixed-sowing machine completes, at one time, stubble flattening and spreading, trenching and soil taking, seed-fertilizer-soil mixing, and discharge of the seed-fertilizer-soil compounds in strips into the ridges.
2) On the seedbed surface between the trenches, the rice stubble and stalks are pressed by using the warped pressing plate installed on the micro-ridge mixed-sowing machine to form a relatively flat underlying surface. The seed-fertilizer-soil compounds are spread in strips on the field surface to complete the sowing. Before falling on the ground, the sown seed-fertilizer-soil compounds pass through the drop guide and the shaper to form trapezoids each with a wide bottom and a narrow top, thereby forming a row of micro-ridges. The ridge has a bottom width of 6.7 cm, a top width of 1.5 cm, and a height of 3.5 cm. During operation, the micro-ridge mixed-sowing machine completes, at one time, stubble flattening and spreading, trenching and soil taking, seed-fertilizer-soil mixing, and discharge of the seed-fertilizer-soil compounds in strips into the ridges. After sowing, irrigation is carried out once in a manner, wherein the manner includes: draining water shortly after the irrigation, without leaving a water layer in the field.
4. When oilseed rape enters the seedling stage, 750 7-week-old young chickens are put per ha for weeding, pest control, disease prevention and control, and intertillage. In the early stage of free-range rearing, the chickens are fed with special feed, with 0.01 kg per day for each chicken. After adapting to the field environment, the chickens obtain food mainly by grazing in the field, supplemented by food feeding. At the bolting stage of oilseed rape, compound feed is put in every late afternoon instead of the special feed. The compound feed is obtained in the following manner: mixing corn flour of 20 kg, bean dregs of 7.5 kg, oil bran of 7.5 kg, rice bran and hull of 7.5 kg, and green feed of 7.5 kg (the green feed shall be chopped) to obtain a mixture, and then adding well water of 25 kg (with probiotics of 0.25 kg) to the mixture. 0.025 kg of feed is put for per chicken each day, and the feeding amount will increase as the weight of the chicken increases.
5. The oilseed rape grew and developed normally during the entire growth period, the yield was increased, and the fertilizer consumption was reduced:

TABLE 1

Comparison table of comprehensive benefits in crop farming by comparing micro-ridge mixed-sowing cultivation with conventional cultivation of oilseed rape

| Type | Consumption of compound fertilizer per ha (kg) | Oilseed rape yield per ha (kg) | Mechanical operation cost per ha (CNY) | Compound fertilizer per ha reduced by (kg) | Mechanical operation cost per ha reduced by (CNY) | Saved cost and increased benefit per ha (CNY) |
|---|---|---|---|---|---|---|
| Micro-ridge mixed-sowing | 300 | 2337 | 2400 | 75 | 600 | 1809 |
| Conventional cultivation | 375 | 2134.5 | 3000 | | | |

What is claimed is:

1. A method for a micro-ridge mixed-sowing cultivation of dryland crops, comprising the following steps:
S1: cleaning ditches at a maturity stage of a preceding crop and draining away water in a dryland;
S2: harvesting the preceding crop, leaving standing stubble, smashing stalks of the preceding crop to obtain smashed stalks, and then spreading the smashed stalks on the standing stubble;
S3: trenching the dryland to form a plurality of ecological trenches, composed of a trench body, side cracks, and bottom mud; and
S4: flattening the standing stubble and the smashed stalks on a seedbed surface to form an underlying surface; molding seed-fertilizer-soil compounds into a ridge shape and falling the seed-fertilizer-soil compounds on the underlying surface to form a plurality of ecological ridges, wherein ecological ridges of the plurality of ecological ridges are formed between adjacent ecological trenches of the plurality of ecological trenches, an ecological depression, composed of a sponge layer, topsoil layer, and ecological cracks, is formed between adjacent ecological ridges of the plurality of ecological ridges, sowing, and after sowing, an irrigation is carried out once in a manner, wherein the manner comprises: draining irrigation water shortly after the irrigation, without leaving a water layer in a field; wherein the seed-fertilizer-soil compounds are obtained by thoroughly mixing soil with seeds of the dryland crops and chemical fertilizers.

2. The method according to claim 1, wherein
in S4, each ecological ridge of the plurality of ecological ridges is a trapezoid with a bottom width of 5.5 cm to 11.5 cm, a top width of 1.5 cm to 5.5 cm, and a height of 3.5 cm to 9.5 cm.

3. The method according to claim 2, wherein
in S3, a chain trencher is used for trenching the dryland;
in S4, the standing stubble and the smashed stalks are flattened by using a warped pressing plate; and
in S4, the seed-fertilizer-soil compounds pass through a drop guide before falling to the underlying surface, the drop guide conveys the seed-fertilizer-soil compounds to a shaper, and the trapezoid is formed through the shaper to fall on the underlying surface, wherein the seed-fertilizer-soil compounds are scattered.

4. The method according to claim 2, wherein
an amount of the seeds in S4 is 3 kg/ha to 105 kg/ha.

5. The method according to claim 2, wherein
the soil in S4 is soil thrown up during trenching in S3.

6. The method according to claim 2, wherein
in S1, trench cleaning and drainage are carried out at a maturity stage of the preceding crop until the dryland is in a state allowing a harvester to operate.

7. The method according to claim 2, further comprising
S5: within 15 days to 50 days after seedling emergence of the dryland crops, putting 600 to 900 6-to-8-week-old young chickens with blindfolds per ha, and
feeding the 600 to 900 6-to-8-week-old young chickens with feed at an early stage of free-range rearing; wherein
after adapting to an environment of the dryland, the 600 to 900 6-to-8-week-old young chickens obtain food mainly by grazing in the dryland, supplemented by food feeding.

8. The method according to claim 1, wherein
in S4, a mass ratio of the seeds of the dryland crops, the chemical fertilizers and the soil is 6 to 14:50 to 70:6,000 to 20,000.

9. The method according to claim 8, wherein
an amount of the seeds in S4 is 3 kg/ha to 105 kg/ha.

10. The method according to claim 8, wherein
the soil in S4 is soil thrown up during trenching in S3.

11. The method according to claim 8, wherein
in S1, trench cleaning and drainage are carried out at a maturity stage of the preceding crop until the dryland is in a state allowing a harvester to operate.

12. The method according to claim 1, wherein
in S3, a spacing between the adjacent ecological trenches is 2 m to 6 m, and
each ecological trench of the plurality of ecological trenches has a depth of 45 cm to 85 cm and a width of 10 cm to 18 cm.

13. The method according to claim 12, wherein
an amount of the seeds in S4 is 3 kg/ha to 105 kg/ha.

14. The method according to claim 12, wherein
the soil in S4 is soil thrown up during trenching in S3.

15. The method according to claim 12, wherein
in S1, trench cleaning and drainage are carried out at a maturity stage of the preceding crop until the dryland is in a state allowing a harvester to operate.

16. The method according to claim 1, wherein
an amount of the seeds in S4 is 3 kg/ha to 105 kg/ha.

17. The method according to claim 1, wherein
the soil in S4 is soil thrown up during trenching in S3.

18. The method according to claim 1, wherein
in S1, trench cleaning and drainage are carried out at a maturity stage of the preceding crop until the dryland is in a state allowing a harvester to operate.

19. The method according to claim 1, further comprising
S5: within 15 days to 50 days after seedling emergence of the dryland crops, putting 600 to 900 6-to-8-week-old young chickens with blindfolds per ha, and
feeding the 600 to 900 6-to-8-week-old young chickens with feed at an early stage of free-range rearing; wherein
after adapting to an environment of the dryland, the 600 to 900 6-to-8-week-old young chickens obtain food mainly by grazing in the dryland, supplemented by food feeding.

20. The method according to claim 1, wherein
a spacing within and between rows of the dryland crops during cultivation is 5 cm to 45 cm×10 cm to 80 cm, and a spacing within and between the rows of the dryland crops during seedling cultivation is 1 cm to 3 cm×2 cm to 6 cm.

* * * * *